United States Patent
Kim et al.

(10) Patent No.: US 11,998,571 B2
(45) Date of Patent: Jun. 4, 2024

(54) PHARMACEUTICAL COMPOSITION COMPRISING STEM CELL-CONDITIONED MEDIUM AND EXOSOME ISOLATED THEREFROM AS ACTIVE INGREDIENT FOR PREVENTION OR TREATMENT OF OCULAR DISEASE

(71) Applicant: DESIGNED CELLS CO., LTD., Chungcheongbuk-do (KR)

(72) Inventors: Yun Bae Kim, Sejong-si (KR); Ehn Kyoung Choi, Daejeon (KR); Tae Myoung Kim, Cheongju-si (KR)

(73) Assignee: DESIGNED CELLS CO., LTD., Chungcheongbuk-do (KR)

( * ) Notice: Subject to any disclaimer, the term of this patent is extended or adjusted under 35 U.S.C. 154(b) by 0 days.

(21) Appl. No.: 18/046,719

(22) Filed: Oct. 14, 2022

(65) Prior Publication Data
US 2023/0134557 A1    May 4, 2023

(30) Foreign Application Priority Data

Nov. 2, 2021 (KR) .......................... 10-2021-0148469
Sep. 1, 2022 (KR) .......................... 10-2022-0110631

(51) Int. Cl.
| | | |
|---|---|---|
| A61K 35/50 | (2015.01) | |
| A23L 33/10 | (2016.01) | |
| A61K 9/127 | (2006.01) | |
| A61P 27/02 | (2006.01) | |
| A61P 27/06 | (2006.01) | |
| C12N 5/073 | (2010.01) | |

(52) U.S. Cl.
CPC .............. *A61K 35/50* (2013.01); *A23L 33/10* (2016.08); *A61K 9/127* (2013.01); *A61P 27/02* (2018.01); *A61P 27/06* (2018.01); *C12N 5/0605* (2013.01); *A23V 2002/00* (2013.01); *C12N 2500/02* (2013.01)

(58) Field of Classification Search
None
See application file for complete search history.

(56) References Cited

U.S. PATENT DOCUMENTS

| | | | |
|---|---|---|---|
| 8,474,978 B2 * | 7/2013 | Huang ................... | G06T 7/0012 351/246 |
| 10,167,448 B2 | 1/2019 | Chang et al. | |
| 10,238,692 B2 | 3/2019 | Yang et al. | |
| 11,524,036 B2 | 12/2022 | Lew et al. | |
| 2009/0238801 A1 * | 9/2009 | Woodbury .............. | C12N 5/067 435/378 |
| 2014/0341882 A1 | 11/2014 | Ochiya | |
| 2015/0231180 A1 * | 8/2015 | Du ......................... | A61P 27/02 424/93.7 |
| 2022/0409671 A1 * | 12/2022 | Kim ....................... | A61P 27/04 |

FOREIGN PATENT DOCUMENTS

| | | |
|---|---|---|
| KR | 10-2006-0062688 | 6/2006 |
| KR | 10-1091117 | 12/2010 |
| KR | 10-2017-0044999 | 4/2017 |
| KR | 10-2018-0131158 | 12/2018 |
| KR | 10-2019-0066885 | 6/2019 |
| KR | 10-2019-0092978 | 8/2019 |
| KR | 20210066636 A * | 11/2019 |
| KR | 10-2021-0066636 | 6/2021 |

OTHER PUBLICATIONS

McManes et al., 2020 (allaboutvision.com/conditions/glaucoma-prevention/). (Year: 2020).*
Jeong, et al., "Extracellular Vesicles Released from Neprilysin Gene-Modified Human Umbilical Cord-Derived Mesenchymal Stem Cell Enhance Therapeutic Effects in an Alzheimer's Disease Animal Model" Stem Cells International, 2021, vol. 2021, pp. 1-20.
KR 10-2017-0044999, "Composition for improving skin and preventing hairloss and method for preparing the same," Apr. 26, 2017, English language translation of abstract, 1 page.
KR 10-2018-0131158, "Method for stimulating the secretion of exosome by stem cell and cosmetic composition comprising thereof," Dec. 10, 2018, English language machine translation of abstract, Espacenet, date obtained: Feb. 7, 2023, 1 page.
KR 10-2019-0066885, "Composition for treating or preventing arthritis comprising culture solution of stem cell-derived exosome," Jun. 14, 2019, English language translation of abstract, 1 page.
KR 10-2019-0092978, "Pharmaceutical composition for preventing or treating neurodegenerative disease comprising turbinate mesenchymal stem cell as an active ingredient," Aug. 8, 2019, English language machine translation of abstract, Espacenet, date obtained: Feb. 7, 2023, 1 page.
KR 10-2021-0066636, "Pharmaceutical composition for preventing and treating optic nerve disease," Jun. 7, 2021, English language translation of abstract, 1 page.
"Membrane metallo-endopeptidase [Homo sapiens]," NCBI, GenBank accession No. AAI01633.1 (2007).
Shigematsu, et al., "Hypothesis: Intravenous administration of mesenchymal stem cells is effective in the treatment of Alzheimer's disease" Medical Hypotheses, 2021, vol. 150, pp. 1-3.

* cited by examiner

*Primary Examiner* — Celeste A Roney
(74) *Attorney, Agent, or Firm* — Hoxie & Associates LLC

(57) ABSTRACT

Disclosed herein is a pharmaceutical composition comprising at least one selected from the group consisting of a stem cell-conditioned medium and an exosome isolated therefrom as an active ingredient for prevention or treatment of an ocular disease. Containing exosomes, growth factors and neurotrophic factors at high levels and functioning to: promote retinal cell proliferation and wound recovery; protect retinal cells against oxidative stress or hypoxia; lower the increased intraocular pressure and restore the atrophy of the retinal layer and the retinal ganglion cell layer to normal levels in the glaucoma animal model; and have a protective effect on retinal ganglion cells and nerve cells, the stem cell-conditioned medium according to the present disclosure can find advantageous applications in the therapy of an ocular disease.

4 Claims, 13 Drawing Sheets

[Fig. 1]
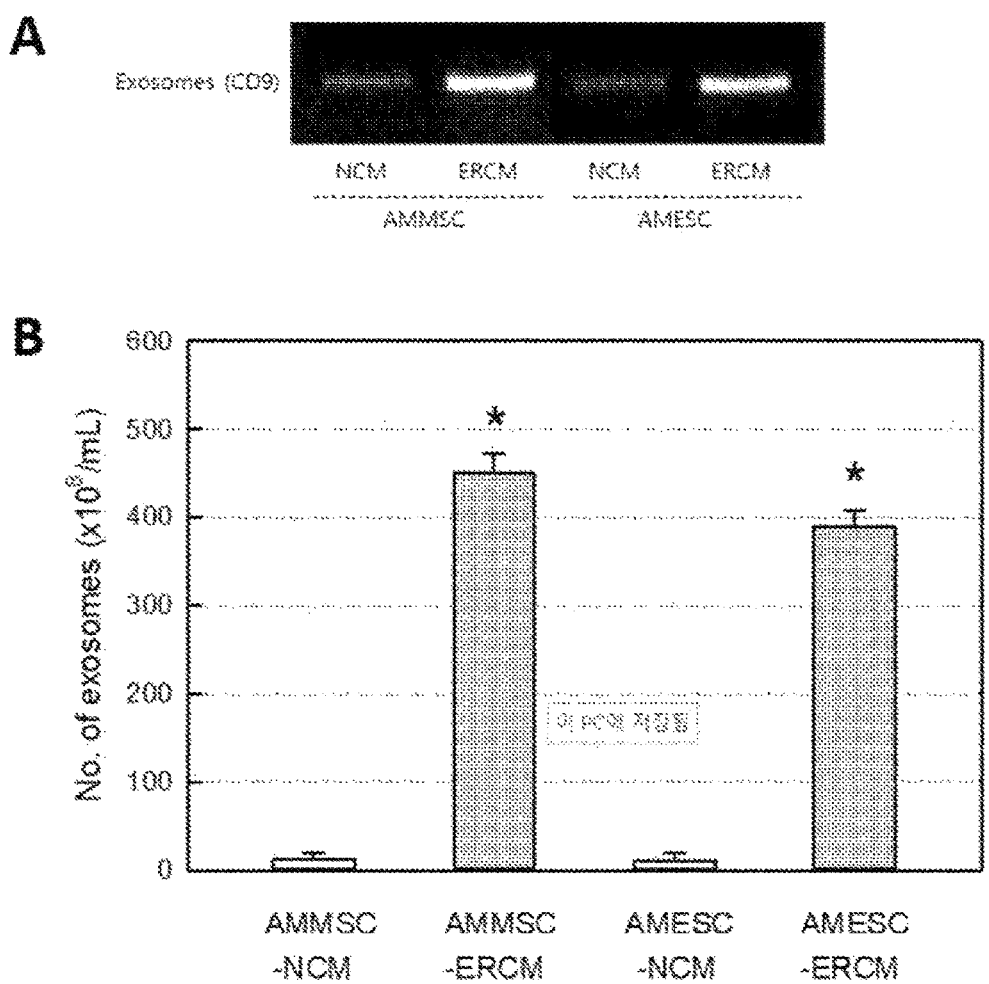

[Fig. 2]
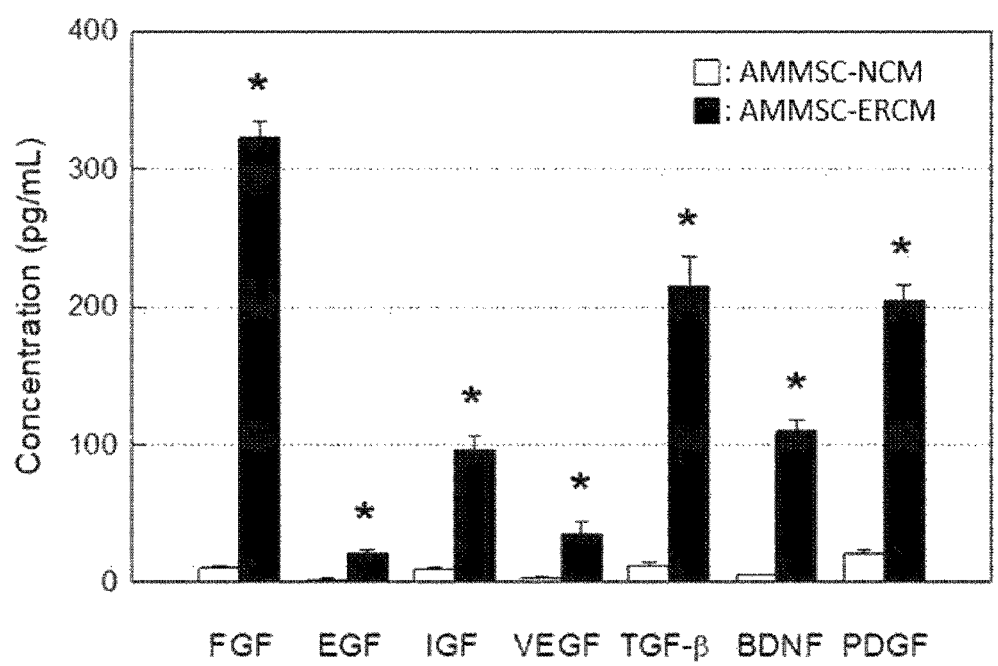

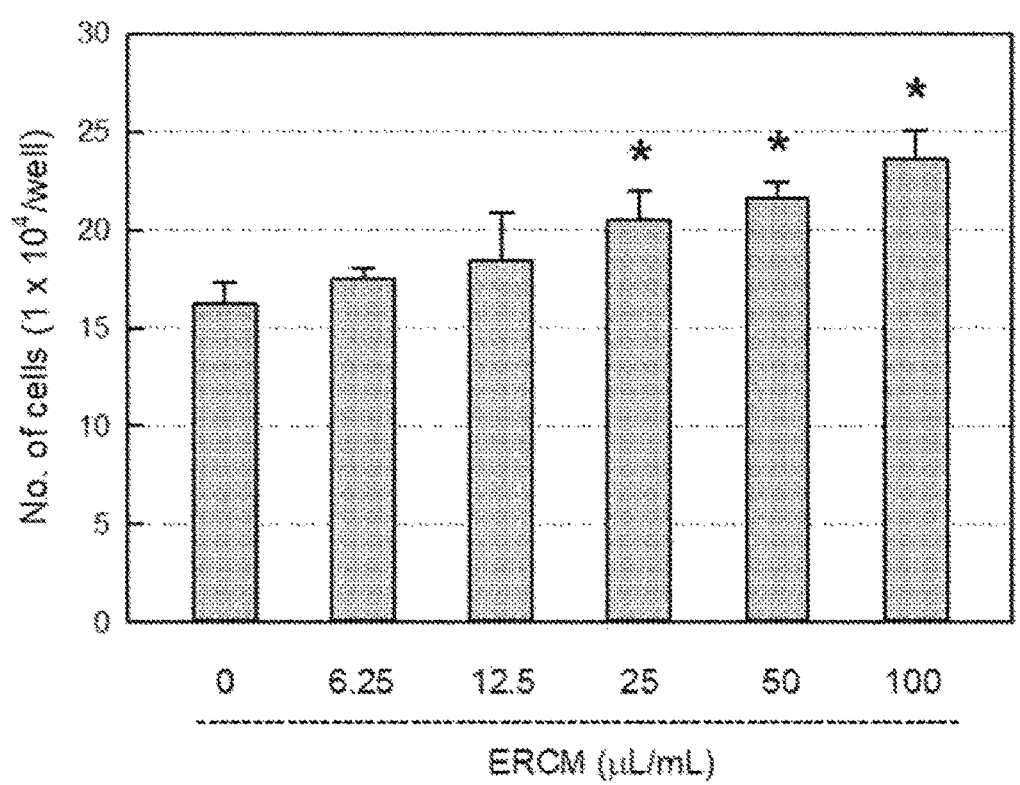
[Fig. 3]

[Fig. 4]
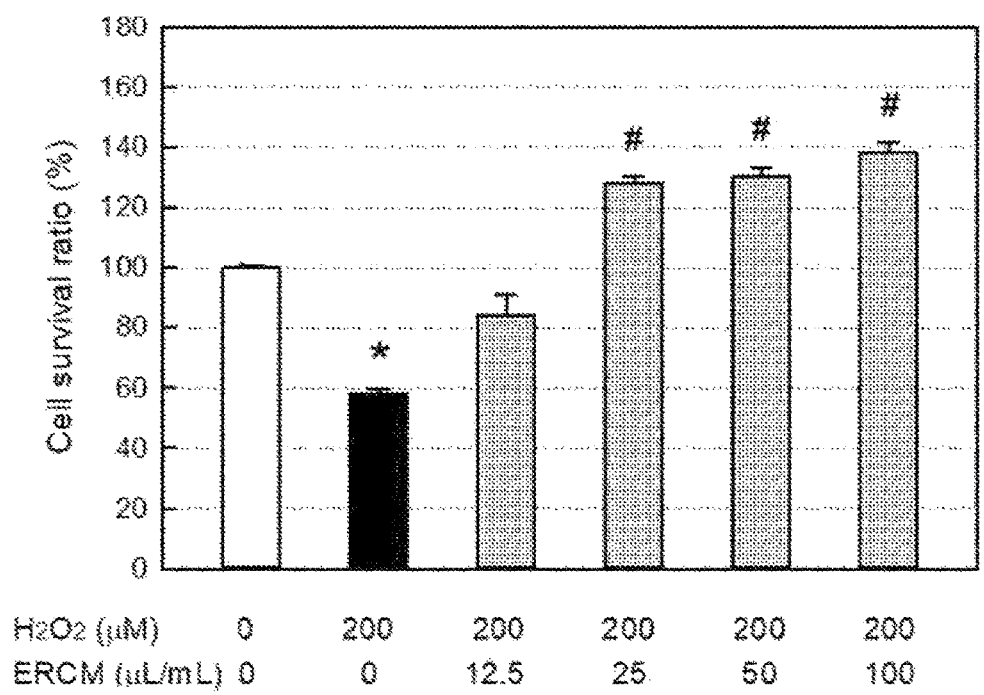

[Fig. 5]
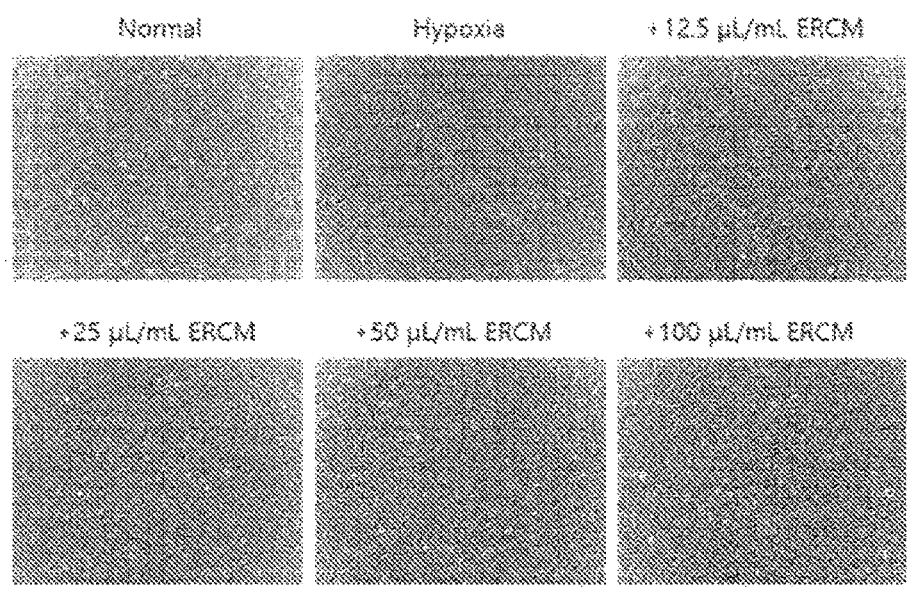
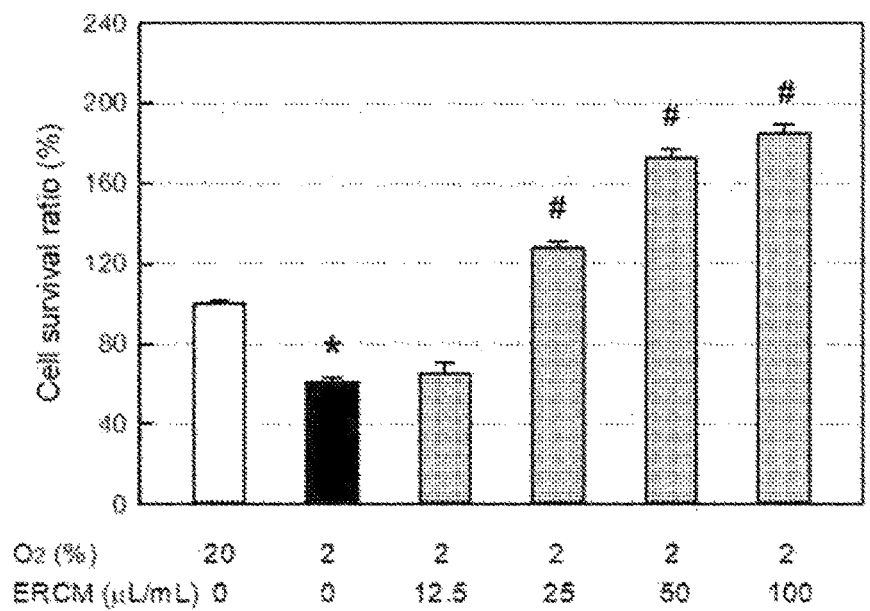

[Fig. 6]
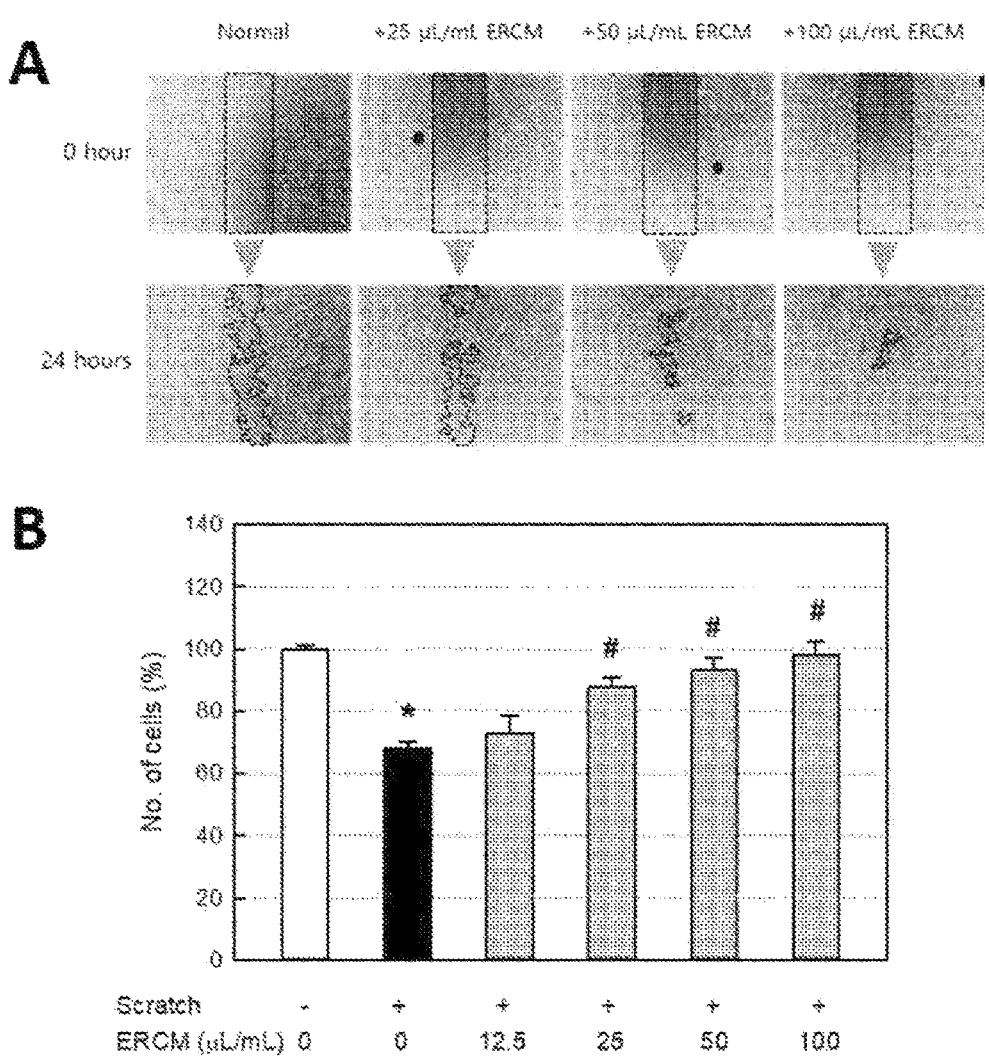

[Fig. 7]
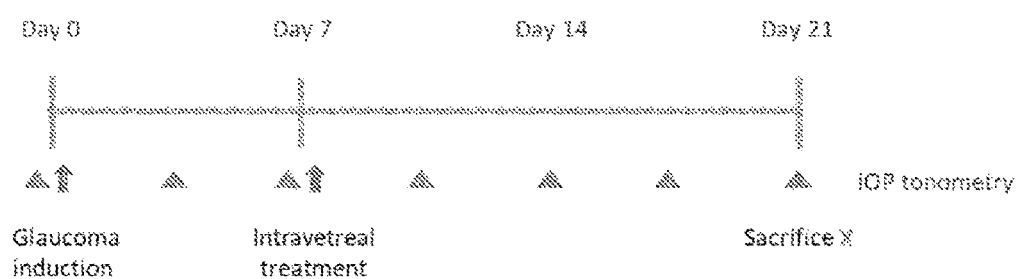

[Fig. 8]
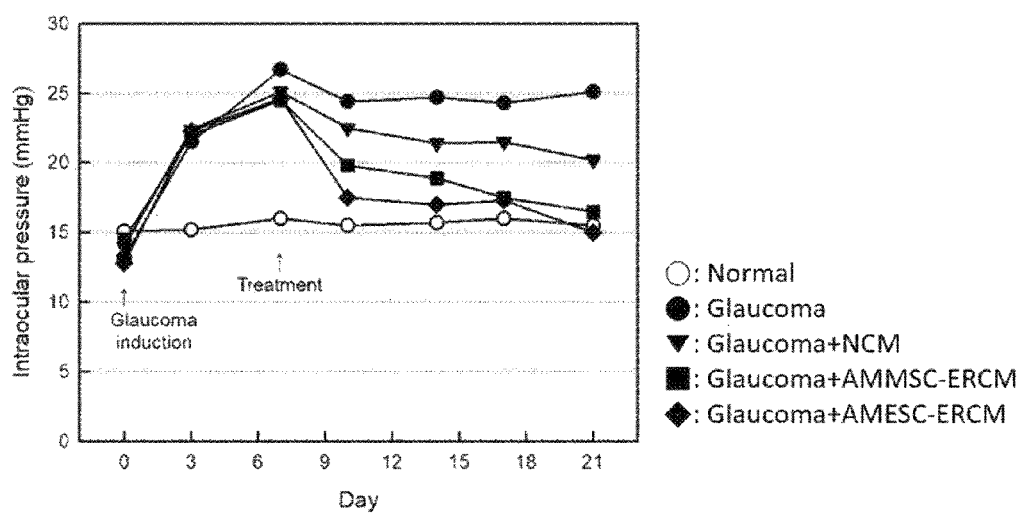

[Fig. 9]
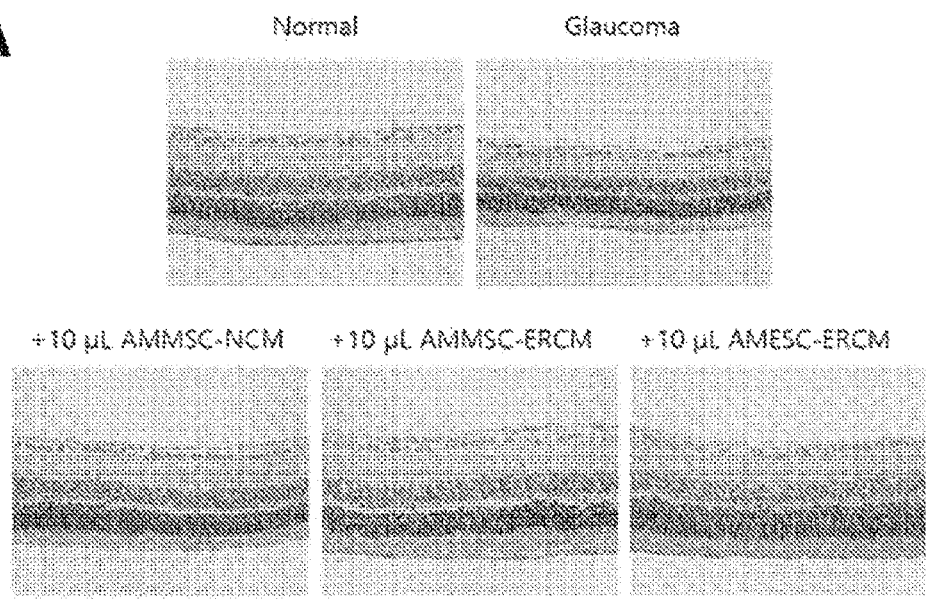
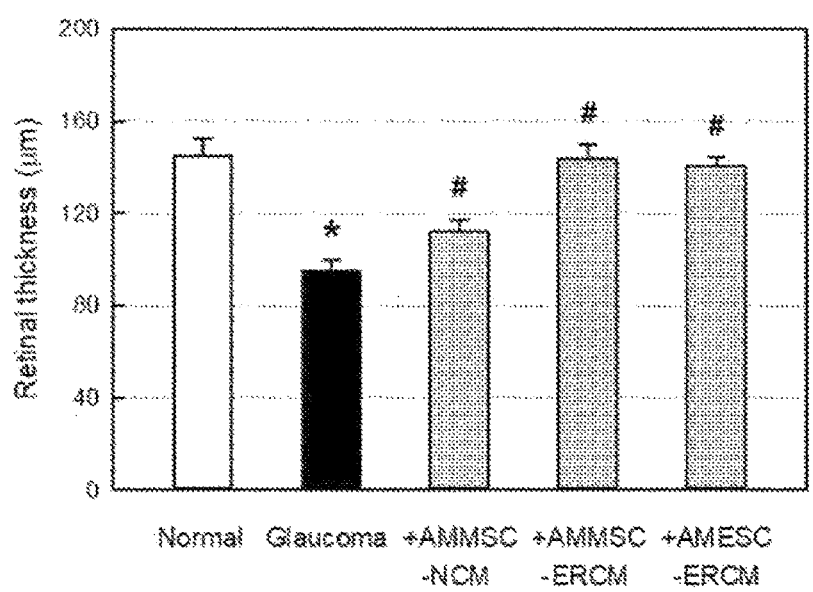

[Fig. 10]
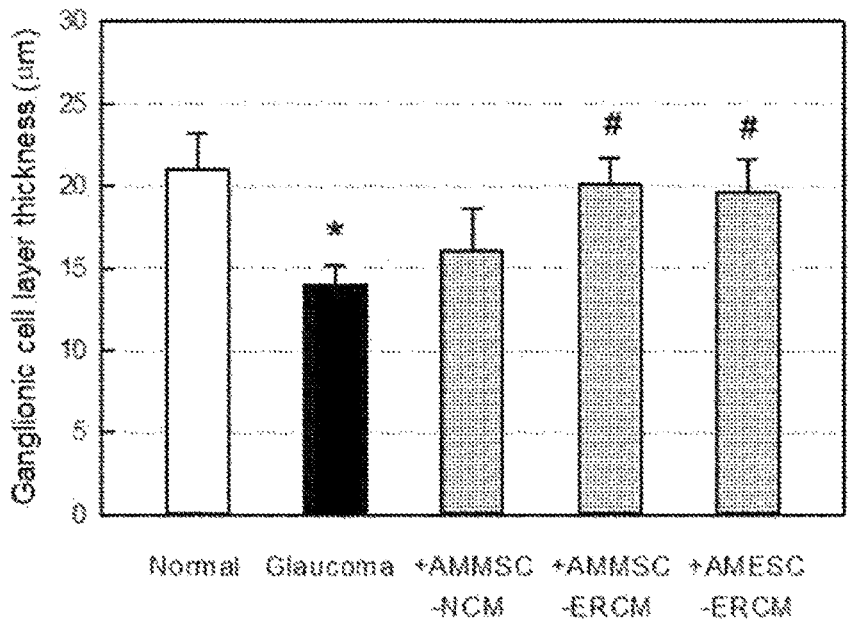
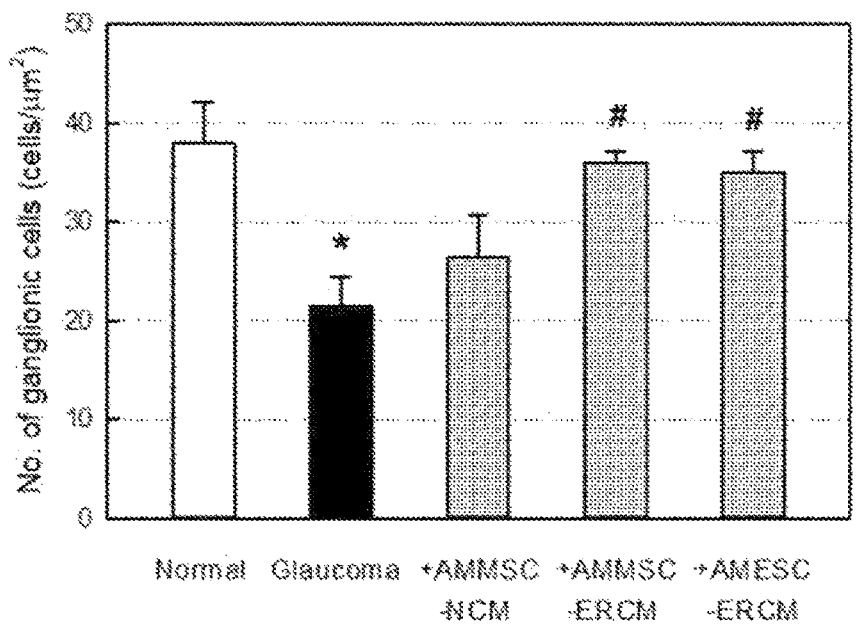

[Fig. 11]
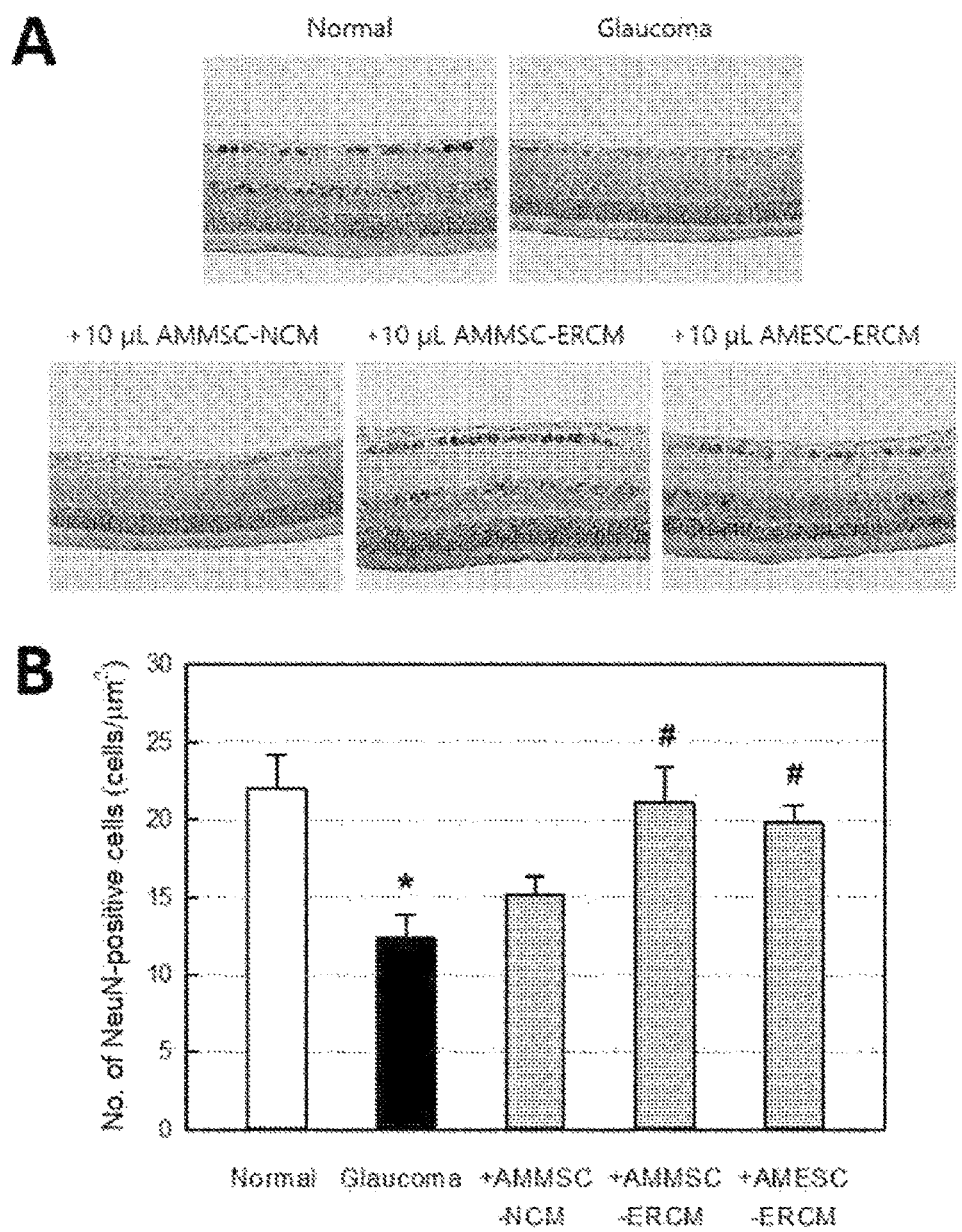

[Fig. 12]
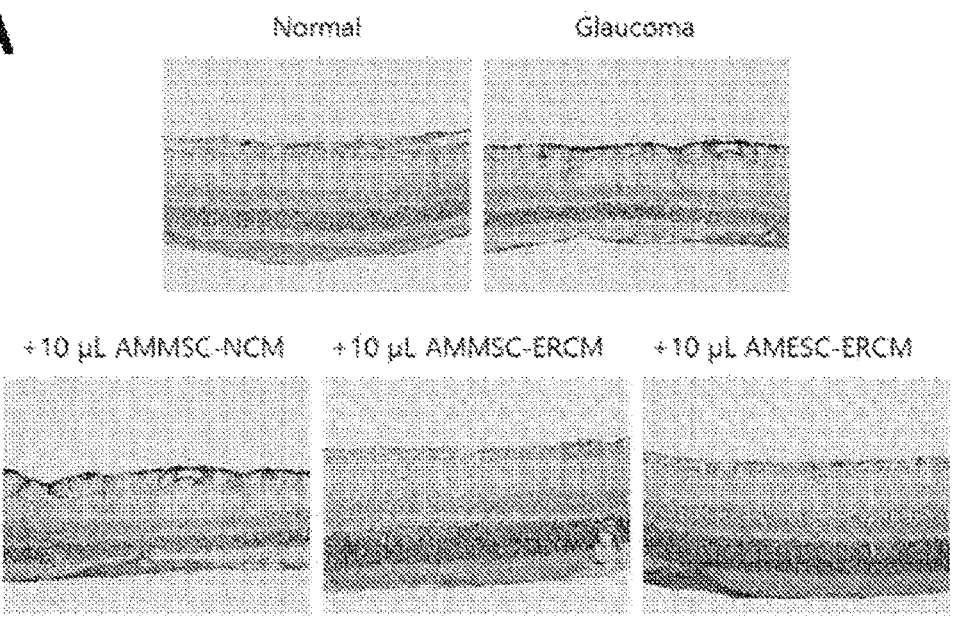
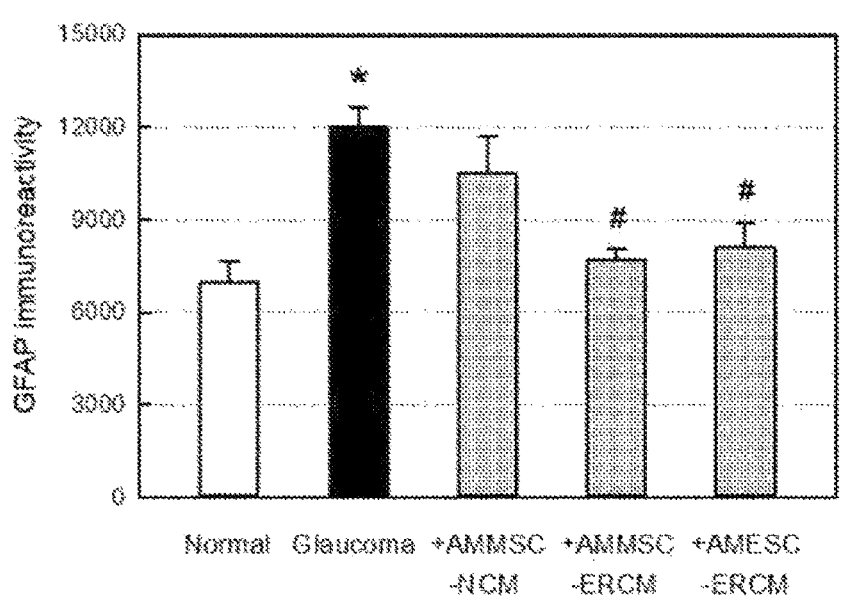

[Fig. 13]
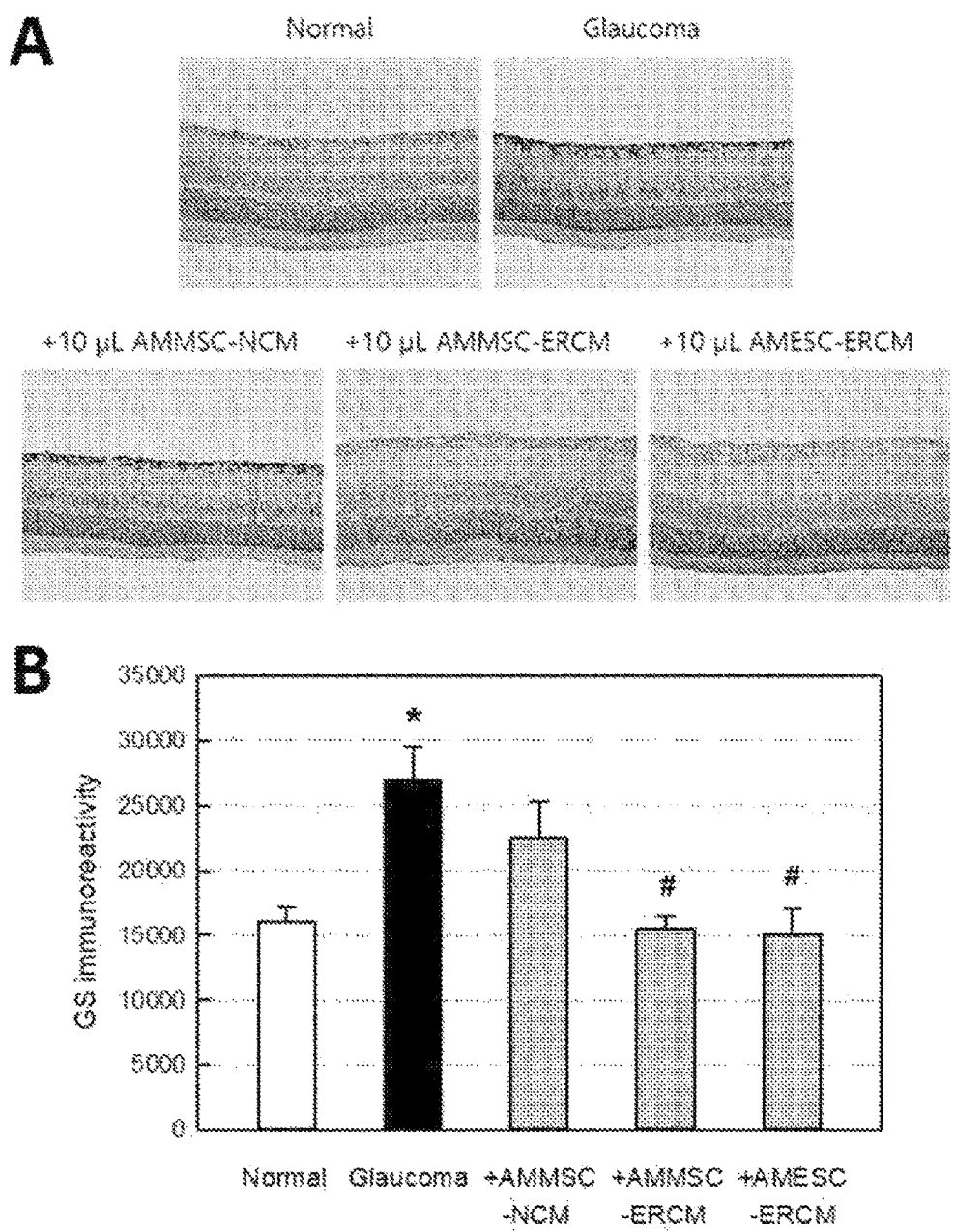

PHARMACEUTICAL COMPOSITION COMPRISING STEM CELL-CONDITIONED MEDIUM AND EXOSOME ISOLATED THEREFROM AS ACTIVE INGREDIENT FOR PREVENTION OR TREATMENT OF OCULAR DISEASE

CROSS-REFERENCE TO RELATED APPLICATIONS

This application is a US. national application filed under 35 U.S.C. § 111(a), which claims benefit to and priority of Korean Patent Application Nos. 10-2021-0148469, filed on Nov. 2, 2021, and 10-2022-0110631, filed on Sep. 1, 2022, the contents of each of which are hereby incorporated by reference in its entirety.

BACKGROUND OF THE INVENTION

1. Field of the Invention

The present disclosure relates to a pharmaceutical composition comprising a stem cell-conditioned medium and an exosome isolated therefrom as an active ingredient for prevention or treatment of an ocular disease.

2. Description of the Prior Art

The retina of the eye is an organ belonging to the central nervous system, and mature retinal cells, like most neuronal cells in the brain, do not divide under normal conditions. Decreasing in function of retinal cells readily leads to abnormality in the vision and makes aging of the eye rapidly proceed. Oxidative stress is the most well-known cause of deterioration of retinal cell function. This is because tissues including the retina, optic nerve, photoreceptor cells, and lens, which are constituents of the eyeball, are constantly exposed to light and ultraviolet rays, undergoing oxidative damage therefrom. The oxidative damage causes modifications in cell constituents including DNA, proteins, lipids, etc., and induces cell death, resulting in ocular aging. Such ocular aging causes serious eye diseases such as retinal geographic atrophy, diabetic retinopathy, cataract, glaucoma, and dry eye.

Glaucoma, which is one of the diseases caused by aging of the eye, occurs in the optic nerve including retinal plexus cells while appearing in the form of retinal layer and optic nerve atrophy. Untreated glaucoma may result in permanent visual impairment. In the past, glaucoma was defined as a disease in which damage to the optic nerve and other visual field disturbances are caused by higher-than-normal pressure in the eye, but is recently defined as progressive optic neuropathy in which characteristic changes in the optic nerve and visual field disturbance are caused by not only high intraocular pressure, but also various other factors involved in glaucoma optic nerve damage.

Glaucoma is usually treated with drug or laser therapy to control intraocular pressure. If visual field disturbance and glaucoma optic nerve changes continue despite these therapies, surgical treatment is performed. For surgical treatment, however, antimetabolites such as 5-fluorouracil (5-FU) or mitomycin (MMC) were used as supplemental agents to increase the surgical success rate, but with the consequent increased onset of surgical complications such as low intraocular pressure, bleb leakage, and bleb-related infection. Accordingly, there is a need for a method for treating glaucoma as an alternative to surgical treatment. In this regard, reference may be referred to Korean Patent Publication Number 10-2020-0137499, which pertains to a peptide for preventing or treating glaucoma, disclosing that the peptide composed of a specific amino acid sequence can be used for treating glaucoma by inhibiting the apoptosis of retinal ganglion cells, the dent or degeneration of optic nerve papilla tissues, retinal ganglion cell loss in the retinal ganglion cell layer, and the activity of the astrocytes or microglia excessively activated by damage to the optic nerve.

SUMMARY OF THE INVENTION

The present disclosure aims to provide a use of a stem cell-conditioned medium and an exosome isolated therefrom.

In order to accomplish the aim, the present disclosure provides a pharmaceutical composition containing at least one selected from the group consisting of a stem cell-conditioned medium and an exosome isolated therefrom as an active ingredient for prevention or treatment of an ocular disease.

In addition, the present disclosure provides a health functional food containing at least one selected from the group consisting of a stem cell-conditioned medium and an exosome isolated therefrom as an active ingredient for prevention or alleviation of an ocular disease.

Furthermore, the present disclosure provides a method for preventing, alleviating, or treating an ocular disease, the method including a step of administering to a subject at least one selected from the group consisting of a stem cell-conditioned medium and an exosome isolated therefrom.

Moreover, the present disclosure provides a use of at least one selected from the group consisting of a stem cell-conditioned medium and an exosome isolated therefrom for preparing a medicinal agent for prevention, alleviation, or treatment of an ocular disease.

Containing exosomes, growth factors and neurotrophic factors at high levels and functioning to: promote retinal cell proliferation and wound recovery; protect retinal cells against oxidative stress or hypoxia; lower the increased intraocular pressure and restore the atrophy of the retinal layer and the retinal ganglion cell layer to normal levels in the glaucoma animal model; and have a protective effect on retinal ganglion cells and nerve cells, the stem cell-conditioned medium according to the present disclosure can find advantageous applications in the therapy of an ocular disease.

BRIEF DESCRIPTION OF THE DRAWINGS

The above and other aspects, features and advantages of the present disclosure will be more apparent from the following detailed description taken in conjunction with the accompanying drawings, in which:

FIG. 1 shows images of the exosomal marker CD9 expressed (A) and counts of the exosomes (B) in the normal conditioned medium (NCM), or exosome-rich conditioned medium (ERCM) of amniotic membrane mesenchymal stem cells (AMMSC) or amniotic membrane epithelial stem cells (AMESC) obtained in an embodiment of the present disclosure;

FIG. 2 is a graph illustrating the expression of growth factors and neurotrophic factors in the normal conditioned medium (NCM) or exosome-rich conditioned medium (ERCM) of amniotic membrane mesenchymal stem cells (AMMSC) or amniotic membrane epithelial stem cells (AMESC) obtained in an embodiment of the present disclosure;

FIG. 3 is a graph demonstrating that the exosome-rich conditioned medium of amniotic membrane mesenchymal stem cells (AMMSC) obtained in an embodiment of the present disclosure promotes the growth of retinal cells;

FIG. 4 is a graph demonstrating that the exosome-rich conditioned medium of amniotic membrane mesenchymal stem cells (AMMSC) obtained in an embodiment of the present disclosure protects retinal cells against oxidative stress;

FIG. 5 shows photographic images of retinal cells (A) and a graph of cell viability (B), demonstrating that the exosome-rich conditioned medium of amniotic membrane mesenchymal stem cells obtained in an embodiment of the present disclosure protects retinal cells against hypoxic damage;

FIG. 6 shows photographic images of retinal cells (A) and a graph of cell counts (B), demonstrating that the exosome-rich conditioned medium of amniotic membrane mesenchymal stem cells obtained in an embodiment of the present disclosure has a wound healing effect on retinal cells;

FIG. 7 is a schematic view of an experimental plan using a glaucoma animal model in an embodiment of the present disclosure;

FIG. 8 is a graph demonstrating that the exosome-rich conditioned medium of amniotic membrane mesenchymal stem cells or epithelial stem cells obtained in an embodiment of the present disclosure restores the intraocular pressure in the glaucoma animal model to a normal level.

FIG. 9 shows photographic images of the retinal layer (A) and a graph of the retinal layer thickness (B), demonstrating the amniotic membrane mesenchymal or epithelial stem cell-conditioned medium obtained in an embodiment of the present disclosure restores the retinal layer from a contracted state in a glaucoma animal model;

FIG. 10 shows graphs of the thicknesses of the retinal ganglionic cell layer (A) and the counts of retinal ganglionic cells (B), demonstrating that the amniotic membrane mesenchymal or epithelial stem cell-conditioned medium in an embodiment of the present disclosure restores the retinal ganglionic cell layer from a contracted state in a glaucoma animal model.

FIG. 11 shows photographic images of the NeuN protein expression level in retinal layer (A) and a graph of counts of NeuN protein positive retinal cells (B), demonstrating that the amniotic membrane mesenchymal or epithelial stem cell-conditioned medium in an embodiment of the present disclosure increases the expression level of NeuN protein in the glaucoma animal model;

FIG. 12 shows photographic images of the GFAP protein expression level in retinal layer (A) and a graph of counts of GFAP protein positive retinal cells (B), demonstrating that the amniotic membrane mesenchymal or epithelial stem cell-conditioned medium in an embodiment of the present disclosure decreases the expression level of GFAP protein which was elevated in a glaucoma animal model; and FIG. 13 shows photographic images of the GS protein expression level in retinal layer (A) and a graph of counts of GS protein positive retinal cells (B), demonstrating that the amniotic membrane mesenchymal or epithelial stem cell-conditioned medium according to an embodiment of the present disclosure decreases the expression level of GS protein which was elevated in a glaucoma animal model.

DETAILED DESCRIPTION OF THE EXEMPLARY EMBODIMENTS

Below, a detailed description will be given of the present disclosure.

The present disclosure provides a pharmaceutical composition containing at least one selected from the group consisting of a stem cell-conditioned medium and an exosome isolated therefrom as an active ingredient for prevention or treatment of an ocular disease.

As used herein, the term "stem cell" refers to an undifferentiated cell under relatively less development, which retains the potential to differentiate into a cell of a specific tissue. Stem cells can be classified into pluripotent stem cells, multipotent stem cells, and unipotent stem cells based on differentiation potency. In addition, their origins divide the stem cells into embryonic stem cells, adult stem cells, and induced pluripotent stem cells (iPSCs) that are produced from human somatic cells. Specifically, the stem cells according to the present disclosure may be adult stem cells. As used herein, the term "adult stem cells" refers to undifferentiated cells, found in adult tissues or organs, that retain the ability to differentiate into desired cells and self-renew. For instance, the stem cells according to the present disclosure may be amnion-derived adult stem cells, and specifically, the amnion-derived adult stem cells may be at least one selected from the group consisting of amnion-derived mesenchymal stem cells and epithelial stem cells.

The stem cell-conditioned medium according to the present disclosure may be obtained by culturing stem cells in a hypoxic condition. The hypoxic condition may be an oxygen concentration less than about 20%, which is an average oxygen condition in a normal atmosphere. Specifically, the hypoxic condition may be an oxygen concentration of 10% or less, 0.1 to 10%, 0.1 to 8%, 0.1 to 5%, 0.1 to 4%, 1 to 10%, 1 to 8%, 1 to 5%, 1 to 4%, 2 to 10%, 2 to 8%, 2 to 5% or 2 to 4%. In addition, the culturing may be carried out for 1 to 80 hours, 1 to 70 hours, 1 to 60 hours, 1 to 50 hours, 10 to 80 hours, 10 to 70 hours, 10 to 60 hours, 10 to 50 hours, 20 to 80 hours, 20 to 70 hours, 20 to 60 hours, 20 to 50 hours, 30 to 80 hours, 30 to 70 hours, 30 to 60 hours, 30 to 50 hours, 40 to 80 hours, 40 to 70 hours, 40 to 60 hours or 40 to 50 hours.

The stem cell-conditioned medium acquired as in the foregoing may contain a higher level of exosomes compared to cultures acquired in typical conditions. In order words, the stem cell-conditioned medium may be an exosome-rich conditioned medium (ERCM). The term "exosome-rich conditioned medium" (ERCM) refers to a cultured medium of the stem cells having the aforementioned characteristics. That is, the pharmaceutical composition according to the present disclosure can attain the desired effect through not only the stem cell-conditioned medium, but also exosomes contained therein.

As used herein, the term "exosome" refers to an extracellular vesicle (EV) secreted in the form of a membrane structure from various types of cells. Exosomes with an average diameter of about 50 to 200 nm fuse to different cells or tissues and function to deliver membrane components, proteins, RNA, etc. The exosomes may be identified using a marker protein contained therein. The marker protein may be any of the marker proteins known in the art. For example, the marker protein may be CD9 protein.

The stem cell-conditioned medium according to the present disclosure may be filtered or enriched, as necessary, to remove impurities. A method of isolating the exosomes from the stem cell-conditioned medium is also apparent in the art.

The method may be carried out in an appropriately modified manner by a person skilled in the art as necessary.

As used herein, the term "ocular disease" refers to a disease caused by damage to eyeball constituents such as retina, cornea, optic nerve, eyelid, lens, and the like, due to changes in intraocular pressure, lack of oxygen, oxidative stress, hyperglycemia, dry eye, infection, disturbances of metabolism, waste accumulation, and aging. For instance, the ocular disease is intended to encompass all types of ocular diseases known in the art. By way of example, the ocular disease may be optic nerve atrophy, glaucoma, eye stroke, retinal vessel occlusion, uveitis, optic neuritis, retinitis, keratitis, cataract, blepharitis, optic disc edema, optic neuromyelitis or ischemic optic neuritis.

As used herein, the term "glaucoma" refers to a disease caused by a damage to the optic nerve including retinal plexus cells while appearing in the form of retinal and optic nerve atrophy. In the onset of glaucoma, a high intraocular pressure that causes glaucomatous retina and a damage to the optic nerve, and other various factors are involved. In detail, according to its cause, the glaucoma may include open angle glaucoma, closed angle glaucoma, congenital glaucoma, secondary glaucoma, phacolytic glaucoma, pseudoexfoliation glaucoma, phacomorphic glaucoma, neovascular glaucoma, and steroid-induced glaucoma.

The pharmaceutical composition according to the present disclosure may contain the stem cell-conditioned medium and exosomes isolated therefrom as an active ingredient in an amount of 10 to 95% by weight, based on the total weight thereof. In addition, the pharmaceutical composition of the present disclosure may further contain at least one substance that exhibits a function identical or similar to that of the active ingredient.

The pharmaceutical composition of the present disclosure may include generally used carriers, diluents, excipients, or a mixture thereof. So long as it is suitable for delivering the composition of the present disclosure in vivo, any pharmaceutically acceptable carrier may be used. Examples of the carrier include compounds described in Merck Index, 13$^{th}$ ed., Merck & Co. Inc., saline, sterilized water, Ringer's solution, dextrose solution, maltodextrin solution, glycerol, ethanol, or a mixture thereof. If necessary, a general additive such as an antioxidant, a buffer, and a bacteriostatic agent can be additionally added.

When the composition is formulated, a generally used diluent or excipient, such as a filler, an extender, a binder, a humectant, a disintegrant, a surfactant, etc. may be added.

The composition of the present invention can be formulated into an oral or parenteral preparation. The oral preparations may be in a solid or liquid phase. Examples of the solid formulation include tablets, pills, powders, granules, capsules, and troches, and such a solid formulation may be prepared by adding one or more excipients to the composition. The excipient may be starch, calcium carbonate, sucrose, lactose, gelatin, or a mixture thereof. In addition to the excipients, a lubricant, for example, magnesium stearate, talc, etc., can be used. The liquid formulation may be a suspension, a solution, an emulsion, or a syrup. In this regard, the liquid formulation may contain various excipients, such as wetting agents, sweeteners, aromatics, and preservatives.

Formulations for parenteral administration may include injections, suppositories, respiratory inhalation powders, spray aerosols, powders, eye drops, and creams. The injection may be exemplified by sterile aqueous solutions, non-aqueous solvents, suspending agents, and emulsions. As non-aqueous solvents or suspending agents, propylene glycol, polyethylene glycol, vegetable oil, such as olive oil, or injectable ester such as ethylolate may be used.

Also, the present disclosure provides a health functional composition containing at least one selected from the group consisting of a stem cell-conditioned medium and an exosome isolated therefrom as an active ingredient for prevention or alleviation of an ocular disease.

The stem cell-conditioned medium and the exosomes isolated therefrom which are contained in the health functional food according to the present disclosure may retain the same characteristics as in the foregoing.

The health functional food may be prepared by using the stem cell-conditioned medium and exosomes isolated therefrom, which are an active ingredient, as they are or in combination with a different food or food ingredient. In this regard, the content of the active ingredient used may be determined according to a desired purpose and may generally range from 0.01 to 90 parts by weight based on 100 parts by weight of the entire food.

No particular limitations are imparted to forms and types of the health functional food. In detail, the health functional food may be in the form of tablets, capsules, pulvis, granules, liquids, or pills. The health functional food may contain additional ingredients such as flavorants, sweeteners, and natural carbohydrates. The sweeteners may be natural or synthetic. Examples of the natural sweeteners include thaumatin and stevia extracts. The synthetic sweeteners may be exemplified by saccharin and aspartame. In addition, the natural carbohydrates may be monosaccharides, disaccharides, polysaccharides, oligosaccharides, and sugar alcohols.

In addition to the aforementioned ingredients, the health functional food of the present disclosure may further contain various nutrients, vitamins, electrolytes, flavoring agents, colorants, pectic acid and salts thereof, alginic acid and salts thereof, organic acids, protective colloidal viscosifiers, pH adjuster, stabilizers, antiseptics, glycerin, alcohols, etc. All these ingredients may be added singly or in combination. Those ingredients may be used in an amount of 0.01 to 0.1 parts by weight, based on 100 parts by weight of the composition of the present disclosure.

Furthermore, the present disclosure provides a method for preventing, alleviating, or treating an ocular disease, the method including a step of administering to a subject at least one selected from the group consisting of a stem cell-conditioned medium and an exosome isolated therefrom.

The stem cell-conditioned medium and the exosomes isolated therefrom used in the method for prevention, alleviation, or treatment of an ocular disease according to the present disclosure may have the same characteristics as in the foregoing. In addition, the ocular disease may be as described above.

The subject may be a mammalian and particularly a human.

The administration may be oral or parenteral according to desired purposes. Parenteral administration may be carried out by intraocular, intravitreal, subretinal, intraperitoneal, intrarectal, subcutaneous, intravenous, intramuscular or intrathoracic injection, or with eye drops.

The administration may be injected at a pharmaceutically effective dose. The pharmaceutically effective dose may vary depending on various factors including kinds of disease, severity of disease, the patient's sensitivity to drug, administration time and route, treatment period, drugs to be used simultaneously, etc. For a desired effect, the dose of the ingredient of the present disclosure may range from 0.0001 to 1,000 mg/kg and particularly from 0.001 to 500 mg/kg. The administration may be once or many times a day.

The administration may be alone or in combination with a different therapeutic agent. The combination administration may be conducted sequentially or simultaneously.

Moreover, the present disclosure provides a use of at least one selected from the group consisting of a stem cell-conditioned medium and an exosome isolated therefrom in preparing a medicinal agent for prevention, alleviation, or treatment of an ocular disease.

The stem cell-conditioned medium and the exosomes isolated therefrom used in preparing a medicinal agent for prevention, alleviation, or treatment of an ocular disease according to the present disclosure may have the same characteristics as in the foregoing. In addition, the ocular disease may be as described above.

Below, a better understanding of the present disclosure may be obtained through the following Examples which are set forth to illustrate, but are not to be construed to limit, the present disclosure. Anything that has substantially the same configuration and achieves the same effect as the technical idea described in the claims of the present disclosure falls within the technical scope of the present disclosure.

Example 1. Preparation of Amnion-Derived Stem Cell

Human amniotic membrane mesenchymal stem cells (AMMSC) and amniotic membrane epithelial stem cells (AMESC) were prepared as follows.

First, after deliberation by the Institutional Review Board (IRB) of Korea University Anam Hospital, a consent was obtained from each healthy pregnant women, and amniotic membranes were collected following cesarean section delivery. The collected amniotic tissues were treated with collagenase I and added the same volume of a culture medium containing 10% fetal bovine serum (FBS) before centrifugation at 1,500 rpm for 10 minutes. After the supernatant was decanted, the pellet was washed twice, and the red blood cells were lysed with an RBC lysis buffer. The cells that remained intact in the lysate were suspended in a keratinocyte serum-free medium (SFM, Invitrogen, USA) containing 5% FBS, 100 units/ml penicillin, and 100 mg/ml streptomycin. The suspension was incubated at 37° C. in a 5% $CO_2$ condition while the culture medium was substituted every two or three days with a fresh one. By analyzing the cultured stem cells with a flow cytometry system to identify marker genes, it was found that the stem cells were amniotic membrane mesenchymal stem cells and amniotic membrane epithelial stem cells.

Example 2. Preparation of Exosome-Rich Conditioned Medium

The human amniotic membrane mesenchymal stem cells and epithelial stem cells obtained above were cultured as follows, to enrich the cells and increase the content of exosomes in the conditioned medium.

Briefly, the human amniotic membrane mesenchymal stem cells and epithelial stem cells were suspended in a serum-free medium in a hyper flask (Nunc, USA). The stem cells were cultured for 3 days in a 5% carbon dioxide and 20% oxygen condition. After culturing, conditioned medium was filtered using a bottle-top vacuum filter system (0.22 μm, PES membrane, Corning, USA). The filtrate was 30-fold concentrated using Vivaflow-200 (Sartorius, Germany) and lyophilized to prepare an exosome-rich conditioned medium.

Separately, the human amniotic membrane mesenchymal stem cells and epithelial stem cells were cultured under a 20% oxygen condition to prepare as a normal conditioned medium.

Example 3. Analysis of Exosome Content-(1)

Contents of exosomes in the exosome-rich conditioned medium obtained above were analyzed by identifying the expression of the exosomal marker CD9.

First, exosomes were isolated in a typical manner from the prepared exosome-rich conditioned medium. Protein levels in the isolated exosomes were quantitated using a protein DC assay kit (Bio-Rad Laboratories, USA). Twenty-five micrograms of the proteins were taken and mixed with a 6× denaturation buffer, and then the mixture was incubated at 95° C. for 10 minutes to denature the proteins. The denatured proteins were separated by 12% SDS-polyacrylamide gel electrophoresis and transferred onto an immobilon-P PVDF membrane. To block non-specific binding to an antibody, the membrane was pretreated in 5% skim milk. The pretreated PVDF membrane was washed and incubated overnight with a primary antibody to CD9 protein. After completion of the reaction, the PVDF membrane was washed with a TBS-T buffer containing 0.1% Tween-20 and then incubated with the secondary antibody IgG-HRP-linked whole antibody at room temperature for 1 hour. Thereafter, the PVDF membrane was developed using the ECL plus western blotting detection system (GE Health-Care). Images of the CD9 protein thus detected were taken and are depicted in FIG. 1A.

As shown in FIG. 1A, remarkable increased expression level of CD9 were observed in the media of the amniotic membrane mesenchymal stem cells and amniotic membrane epithelial stem cells cultured in a hypoxic condition.

Example 4. Analysis of Exosome Content-(2)

Contents of exosomes in the exosome-rich conditioned medium obtained above were quantitatively analyzed using the NTA system (Nanosight NS300, NanoSight, England). The contents of the exosomes are depicted in FIG. 1B.

As shown in FIG. 1B, remarkable increased expression levels of exosomes were observed in the media of the amniotic membrane mesenchymal stem cells and amniotic membrane epithelial stem cells cultured in a hypoxic condition. In detail, the conditioned media of the amniotic membrane mesenchymal stem cells and amniotic membrane epithelial stem cells cultured in a hypoxic condition contained $4.5 \times 10^{10}$ exosomes/ml and $3.9 \times 10^{10}$ exosomes/ml, respectively, which were about 50-fold abundant, compared to those cultured in a normoxic condition.

Experimental Example 1. Analysis of Growth Factor and Neurotrophic Factor

Growth factors and neurotrophic factors present in the exosome-rich conditioned medium obtained above were analyzed as follows. In brief, protein expression levels of FGF (fibroblast growth factor), EFG (elongation factor G), IGF (insulin-like growth factor), VEGF (vascular endothelial growth factor), TGF-β (transforming growth factor-β), BDNF (brain-derived neurotrophic factor), and PDGF (platelet-derived growth factor) were measured using ELISA according to the manufacturer's protocol. In this regard, a normal conditioned medium was used as a control.

Expression level measurements of growth factors and neurotrophic factors are depicted in FIG. 2.

As shown in FIG. 2, remarkably increased expression levels of the growth factors and neurotrophic factors were observed in an amniotic membrane mesenchymal stem cell-conditioned mediums incubated in a hypoxic condition.

Experimental Example 2. Promotion of Growth of Retinal Cell

The promotive effect of the stem cell-conditioned mediums on the growth of retinal cells was analyzed as follows.

First, ARPE-19 cells (#CRL2302, ATCC, USA) were seeded at a density of $1\times10^5$ cells/ml into 96-well plates and incubated overnight. The amniotic membrane mesenchymal stem cell-conditioned medium was added in an amount of 0, 6.25, 12.5, 25, 50, or 100 µl/ml to the cultured cells, followed by incubation at 37° C. in a normoxic condition (20% $O_2$). After 24 hours, the cultured cells were counted, and the results are depicted in FIG. 3.

As can be seen in FIG. 3, the amniotic membrane mesenchymal stem cell-conditioned medium promoted the growth of retinal cells in a dose-dependent manner. Particularly, the growth of retinal cells was remarkably increased when the amniotic membrane mesenchymal stem cell-conditioned medium was treated at a concentration of as high as 25 to 100 µl/ml.

Experimental Example 3. Protection of Retinal Cell Against Oxidative Stress

Protective effects of the stem cell-conditioned medium against oxidative stress were examined as follows.

First, ARPE-19 cells were seeded at a density of $1\times10^5$ cells/ml into 96-well plates and incubated overnight. The cultured cells were treated with 200 µM hydrogen peroxide, together with 0, 12.5, 25, 50, or 100 µl/ml of the amniotic membrane stem cell-conditioned medium, followed by incubation at 37° C. in a normoxic condition (20% $O_2$). After 24 hours, the cultured cells were counted. Cell viability was calculated from the count of the cells and the results are depicted in FIG. 4.

As shown in FIG. 4, the cell viability was decreased to about 42% by hydrogen peroxide, but recovered by the amniotic membrane mesenchymal stem cell-conditioned medium. The amniotic membrane mesenchymal stem cell-conditioned medium recovered the cell viability in a dose-dependent manner. Particularly when applied at a concentration of as high as 25 to 100 µl/ml, the amniotic membrane mesenchymal stem cell-conditioned medium completely recovered the cells from oxidative stress-induced damage and rather promoted cell growth, making the cells more abundant, compared to the non-treated control.

Experimental Example 4. Protection of Retinal Cell Against Hypoxia

The stem cell-conditioned medium was examined for a protective effect against hypoxia as follows.

First, ARPE-19 cells were seeded at a density of $1\times10^5$ cells/ml into 96-well plates and incubated overnight. The cultured cells were treated with 0, 12.5, 25, 50, or 100 µl/ml of the amniotic membrane stem cell-conditioned medium, followed by incubation at 37° C. in a hypoxic condition (2% $O_2$). After 24 hours, the cultured cells were counted. Images of the cells were taken during cell growth and are given in FIG. 5A and the cell viability calculated from the counts of the cells are depicted in FIG. 5B. In this regard, cells cultured in a normoxic condition (20% $O_2$) were used as a control.

As shown in FIG. 5, the cell viability of the cells cultured in a hypoxic condition decreased to about 39%, but was recovered by the amniotic membrane mesenchymal stem cell-conditioned medium. The amniotic membrane mesenchymal stem cell-conditioned medium increased the cell viability in a dose-dependent manner. Particularly when applied at a concentration of as high as 25 to 100 µl/ml, the amniotic membrane mesenchymal stem cell-conditioned medium completely recovered the cells from oxidative stress-induced damage and rather promoted cell growth, making the cells more abundant, compared to the non-treated control.

Experimental Example 5. Recovery of Retinal Cell from Wound

The stem cell-conditioned medium was analyzed for activity of recovering retinal cells from wound by a cell migration assay.

First, ARPE-19 cells were seeded at a density of $1\times10^5$ cells/ml into T-75 plates and cultured. When the cells grew to about 90% confluence in the flask, a 5-mm scratch was made with a pipette tip. The cultured cells were treated with 0, 12.5, 25, 50, or 100 µl/ml of the amniotic membrane stem cell-conditioned medium, followed by incubation at 37° C. in a hypoxic condition (2% $O_2$). After 24 hours, the scratched region, images of sites around the remaining scratch were taken and are given in FIG. 6A while the areas of the scratch were calculated and are depicted in FIG. 6B.

As shown in FIG. 6, the scratch made by a pipette tip was covered by about 20% for 24 hours in the non-treated control whereas when treated at 25, 50, or 100 µl/ml, the amniotic membrane mesenchymal stem cell-conditioned medium covered the scratch by up to 88%, 93%, and 98%, respectively.

Experimental Example 6. Therapy of Glaucoma in Animal Model

A therapeutic effect of the stem cell-conditioned medium on glaucoma was examined in glaucoma animal models.

6-1. Preparation of Animal Model and Administration of Drug

Male SD (Sprague-Dawley) rats at 6 weeks of age (Daehan Biolink, Korea) were reared at a constant temperature of 23±2° C. and a relative humidity of 55±10%, with a light/dark cycle of 12/12 hours. In this regard, a standard rodent diet and filtered water were supplied. All procedures for animal experiments were performed after approval in accordance with the Institutional Animal Care and Use Committee (IACUC) of the Chungbuk National University Laboratory Animal Research Center (LARC). Ocular hypertension was surgically introduced into the left eyes of 35 rats to create glaucoma animal models. In brief, Zoletil® (Virbac Korea, Korea) and Rumpun® (Bayer Korea, Korea) were mixed at a volume ratio of 2:1, and the rats were systemically anesthetized by intraperitoneal injection of the mixture at a dose of 2 ml/kg. Then, 1.8 M hypertonic saline was injected into the scleral vein of anesthetized rats with a Hamilton microliter syringe (Hamilton, USA) at a rate of 50 µl/min. After anesthetization of the rats by inhalation of 0.4% isofurane, the intraocular pressure (IOP) of the rats was measured with a TonoLab tonometer (Icare Finland Oy, Finland). One week after indicating the maximum intraocular pressure, 10 μl of the amnion mesenchymal stem cell-conditioned medium or amnion epithelial stem cell-conditioned medium was administered to the vitreous of the rats. In this regard, 0.9% saline was used as a control. For each rat group, administration conditions are given in Table 1, below and animal experiment plans are depicted in FIG. 7.

TABLE 1

| Animal model | Group | Drug treatment | Dose |
|---|---|---|---|
| Normal animal model | Normal control | — | — |
| Glaucoma animal model (1.8M saline) | Negative control | 0.9% Saline | 10 μl |
| | Test group | normal conditioned medium | 10 μl |
| | | Exosome-rich conditioned medium of amniotic membrane mesenchymal stem cells | 10 μl |
| | | Exosome-rich conditioned medium of amniotic membrane epithelial stem cells | 10 μl |

6-2. Suppression of Intraocular Pressure Elevation

The therapeutic effect on glaucoma was examined by measuring the intraocular pressure in the glaucoma animal models. In brief, IOP was measured twice a week at the same time for three weeks from the day the hypertonic saline was administered to the glaucoma animal models, and the results are depicted in FIG. 8.

As shown in FIG. 8, the IOP which was rapidly increased by the injection of hypertonic saline, was significantly decreased to a normal level (10 to 17 mmHg) by the treatment of stem cell-conditioned medium. In particular, the exosome-rich conditioned medium obtained by hypoxic incubation exhibited a more remarkable effect than the normal conditioned medium obtained by normoxic incubation.

6-3. Restoration from Retinal Layer Contraction

The stem cell-conditioned medium-administered glaucoma animal models were sacrificed, and the retinal layer was stained with hematoxylin-eosin before examining whether the retinal layer was restored from a contracted state.

First, the rats were sacrificed with deep anesthetization and the eyeballs were excised. The eyeballs were fixed by immersion for 24 hours in the Davison's solution (BBC Biochemical, USA), washed, and dewatered. The dried eyeballs were embedded into paraffin and sectioned by a microtome (Leica Biosystems, Germany) into 4-μm-thick slices. They were placed on a slide, stained with hematoxylin-eosin, and observed under an optical microscope (Carl Zeiss, Germany). The optical images and the retinal thickness measured from the images are given in FIGS. 9A and 9B, respectively.

As shown in FIG. 9, glaucoma induction contacted the retinal layer by up to about 35%, compared to the normal control. However, treatment with the stem cell-conditioned medium significantly restored the retinal layer from the contraction. In particular, the exosome-rich conditioned medium obtained after hypoxic incubation brought about a more remarkable effect, compared with the normal conditioned medium obtained after normoxic incubation.

6-4. Restoration of Retinal Ganglionic Cell Layer from Contraction

In the same manner and condition as in Experimental Example 6-3, examination was made to see whether the retinal ganglionic cell layer in the glaucoma animal model was restored by the stem cell-conditioned medium from the contraction. The thickness of the ganglionic cell layer and the count of ganglionic cells are measured and the measurements are shown in FIGS. 10A and 10B, respectively.

As can be seen in FIG. 10, the thickness of the retinal ganglionic cell layer and the count of retinal ganglionic cells which were decreased by glaucoma, but significantly restored by the stem cell-conditioned mediums. In particular, the exosome-rich conditioned medium obtained after hypoxic incubation brought about a more remarkable effect, compared with the normal conditioned medium obtained after normoxic incubation.

6-5. Protection of Retinal Ganglionic Cell

To examine protective effects of the stem cell-conditioned mediums on retinal cells, cells existing in the retinal ganglion of the glaucoma animal model were immunostained for neuronal nuclei (NeuN) protein.

First, ocular sections were obtained as in Experimental Example 6-3 and placed on a slide. The slide was treated with 1% hydrogen peroxide for 30 minutes. Thereafter, the tissues were washed with PBS and incubated with a streptavidin-biotin peroxidase complex (LSAB2 kit, Dako, USA) for 20 minutes, followed by pretreatment with normal goat serum (Vectastain Elite ABC kit, Vector Laboratories, USA) for 30 minutes. Subsequently, the sections were incubated overnight at 4° C. with a dilution of the primary monoclonal rabbit antibody (1:1,000, Abcam, England) to NeuN protein. After completion of the reaction, incubation was carried out with a biotinylated secondary antibody (Vectastain Elite ABC kit, Vector Laboratories, USA) at room temperature for an additional one hour. The sections were then washed with PBS and treated for 1 to 2 minutes with DAB (3,3-diaminobenzidine tetrahydrochloride, Novus Biologicals, USA) for color development. The sections were counterstained with Harris hematoxylin before observation under an optical microscope. The optical images are given in FIG. 11A while measurements of counts of the stained cells are depicted in FIG. 11B.

As shown in FIG. 11, the counts of the NeuN-positive retinal cells were reduced by glaucoma, but significantly restored by the stem cell-conditioned mediums. In particular, the exosome-rich conditioned medium obtained after hypoxic incubation brought about a more remarkable effect, compared with the normal conditioned medium obtained after normoxic incubation.

6-6. Protection of Optic Nerve

A protective effect of the stem cell-conditioned mediums on the optic nerve in the glaucoma animal model was examined by analyzing the expression of GFAP (glial fibrillary acidic protein) and GS (glutamine synthetase) proteins. GFAP and GS proteins are constituents of Muller cells and the activation of Muller cells indicate damage to the optic nerve.

The experiment was carried out in the same condition and manner as in Experimental Example 6-5, with the exception of using a polyclonal rabbit antibody (1:500, Millipore, USA) to GFAP protein or a monoclonal rabbit antibody (1:500, Abcam, England) to GS protein, instead of the primary antibody to NeuN protein. Immunostained proteins expressed in the optic nerve were observed under an optical microscope. Optical images of GFAP protein are shown in FIG. 12A and quantitative expression levels of GFAP protein are depicted in FIG. 12B. As for GS protein, its optical images and quantitative expression levels are given in FIGS. 13A and 13B, respectively.

As can be seen in FIGS. 12 and 13, the expression levels of GFAP and GS proteins which were elevated by glaucoma were significantly reduced by the stem cell-conditioned mediums. In particular, the exosome-rich conditioned medium obtained after hypoxic incubation brought about a more remarkable effect, compared with the normal conditioned medium obtained after normoxic incubation.

What is claimed is:

1. A method for alleviating or treating glaucoma, the method including a step of administering to a subject suffering from glaucoma at least one selected from the group consisting of a stem cell-conditioned medium and an exosome isolated therefrom, wherein the stem cells are amnion-derived stem cells, and wherein the amnion-derived stem cells are selected one or more from the group consisting of amniotic membrane-derived mesenchymal stem cells and amniotic membrane-derived epithelial stem cells.

2. The method of claim 1, wherein the stem cell-conditioned medium is obtained by culturing stem cells at an oxygen concentration of 10% or less.

3. The method of claim 2, wherein the stem cell-conditioned medium is obtained by culturing stem cells at an oxygen concentration of 1 to 5%.

4. The method of claim 1, wherein administration of the at least one selected from the group consisting of a stem cell-conditioned medium and an exosome isolated therefrom to the subject decreases intraocular pressure.

* * * * *